(12) United States Patent
Errico et al.

(10) Patent No.: US 11,317,958 B2
(45) Date of Patent: May 3, 2022

(54) SURGICAL FIXATION ASSEMBLY AND METHODS OF USE

(71) Applicant: K2M, Inc., Leesburg, VA (US)

(72) Inventors: Thomas J. Errico, New York, NY (US); Peter Newton, La Jolla, CA (US); Harry Shufflebarger, Jupiter, FL (US); Larry E. McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 231 days.

(21) Appl. No.: 16/498,965

(22) PCT Filed: Mar. 22, 2018

(86) PCT No.: PCT/US2018/023823
§ 371 (c)(1),
(2) Date: Sep. 27, 2019

(87) PCT Pub. No.: WO2018/183088
PCT Pub. Date: Oct. 4, 2018

(65) Prior Publication Data
US 2020/0093527 A1 Mar. 26, 2020

Related U.S. Application Data

(60) Provisional application No. 62/478,712, filed on Mar. 30, 2017.

(51) Int. Cl.
*A61B 17/86* (2006.01)
*A61B 17/70* (2006.01)
*A61B 17/00* (2006.01)

(52) U.S. Cl.
CPC ...... *A61B 17/8685* (2013.01); *A61B 17/7032* (2013.01); *A61B 17/7037* (2013.01); *A61B 17/864* (2013.01); *A61B 17/8635* (2013.01); *A61B 17/7082* (2013.01); *A61B 17/8615* (2013.01); *A61B 2017/00477* (2013.01)

(58) Field of Classification Search
CPC .. A61B 17/686; A61B 17/863; A61B 17/8685
See application file for complete search history.

(56) References Cited

U.S. PATENT DOCUMENTS

| 5,876,402 | A | 3/1999 | Errico et al. |
| 2005/0177166 | A1* | 8/2005 | Timm ................ A61B 17/8685 606/278 |

(Continued)

FOREIGN PATENT DOCUMENTS

| CA | 2765204 C | 12/2014 |
| WO | 99/60949 A2 | 12/1999 |

OTHER PUBLICATIONS

International Search Report for Application No. PCT/US2018/023823 dated Jun. 8, 2018.

*Primary Examiner* — Olivia C Chang
(74) *Attorney, Agent, or Firm* — Lerner, David, Littenberg, Krumholz & Mentlik, LLP

(57) ABSTRACT

A fixation assembly includes a tapered cannula, a post, and a snap ring. The snap ring is attachable to the post and the tapered cannula. The snap ring is configured to maintain the tapered cannula axially fixed in relation to the post such that the tapered cannula and the post are rotatable relative to each other.

19 Claims, 7 Drawing Sheets

(56) References Cited

U.S. PATENT DOCUMENTS

2005/0273105 A1 12/2005 Konieczynski et al.
2006/0235410 A1* 10/2006 Ralph ................ A61B 17/8038
606/313
2011/0106172 A1 5/2011 Wallenstein et al.

* cited by examiner

SURGICAL FIXATION ASSEMBLY AND METHODS OF USE

CROSS-REFERENCE TO RELATED APPLICATIONS

The present application is a national phase entry under 35 U.S.C. § 371 of International Application No. PCT/US2018/023823 filed Mar. 22, 2018, which claims the benefit of U.S. Provisional Patent Application No. 62/478,712, filed Mar. 30, 2017, the entire disclosure of which is incorporated by reference herein.

TECHNICAL FIELD

This disclosure relates generally to spinal surgery. More specifically, the present disclosure relates to surgical fixation assemblies for spinal stabilization and methods of use.

BACKGROUND

Spinal pathologies, whether the result of genetic or developmental irregularities, trauma, chronic stress, tumors, or disease can limit the spine's range of motion or threaten critical elements of the nervous system housed within the spine. A variety of systems to correct the alignment of the spinal vertebrae involving the implantation of artificial assemblies in or on the spine have been devised.

The mechanical hardware used to immobilize the spinal column typically involves a series of bone screws and metal rods or plates. When the spine surgery is performed, it is common practice to place bone screws into the vertebral bodies and then connect a metal rod between the screws, thus creating a rigid structure between adjacent vertebral bodies. In some cases, these devices may be permanently implanted in the patient. In other cases, the devices may be implanted only as a temporary means of stabilizing or fixing the bones or bone fragments, with subsequent removal when no longer needed.

When using screws, the surgeon directs the screw into the vertebral body. Because different patients have different anatomies, there exists the potential for part of the vertebral body to be breached. A breach occurs when the screw protrudes through the bone on either the lateral or medial side. Often, if there is a lateral breach, the surgeon leaves the screw in place. If the breach occurs medially into the spinal canal, the spinal nerves can rub against the threads causing the patient pain and possibly requiring a revision surgery. Typically, when the surgeon recognizes the breach, he uses an instrument to displace the nerves to protect them from damage, removes the original screw and redirects it. Redirection removes more bone and can compromise fixation of the screw or completely damage the vertebral body rendering it unusable as a point of device fixation.

Therefore, a continuing need exists for an improved fixation member that could reduce the time and labor required by a user to insert the fixation member, such as a screw, into a vertebra, while also protecting the spinal nerves and preventing redirection.

SUMMARY

In one aspect, the present disclosure is directed to a fixation assembly that includes a tapered cannula, a post, and a snap ring. The snap ring is attachable to the post and the tapered cannula and is configured to maintain the tapered cannula axially fixed in relation to the post such that the tapered cannula and the post are rotatable relative to each other.

In some embodiments, the tapered cannula may be threaded.

In certain embodiments, the post may define a first ring groove positioned to receive the snap ring therein. The tapered cannula may define a second ring groove positioned to receive the snap ring therein.

In some embodiments, the snap ring may be formed of a flexible material.

In embodiments, the post may support a ledge configured to engage the tapered cannula to limit distal movement of the post relative to the tapered cannula.

In certain embodiments, the tapered cannula may define one or more cut outs in a proximal end portion thereof.

In some embodiments, the post may include a spherical head supported on a proximal end portion thereof.

In embodiments, the post may include a shank having an elliptical cross-section. The shank may extend to a distal tip. The distal tip may have one or more flat surfaces to facilitate insertion of the shank into osseous tissue.

According to another aspect of the present disclosure, a fixation assembly includes a rod-receiving housing and a fixation assembly coupled to the rod-receiving housing. The fixation assembly including a tapered cannula, a post, and a snap ring. The snap ring attachable to the post and the tapered cannula to secure the post and the tapered cannula together.

In accordance with still another aspect of the present disclosure, a method for securing a fixation assembly to osseous tissue is provided. The method includes securing a tapered cannula to hard cortical tissue, proximal and adjacent to the isthmus of a pedicle, inserting a post through the tapered cannula, and axially fixing the post to the tapered cannula with a snap ring.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the present disclosure and, together with a general description of the disclosure given above, and the detailed description of the embodiments given below, serve to explain the principles of the present disclosure, wherein.

DETAILED DESCRIPTION

Figure 1A:
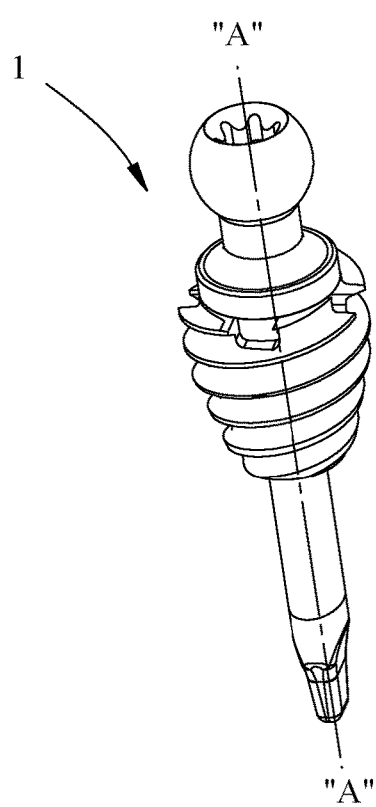
FIG. 1A is an isometric view of a fixation assembly according to the present disclosure.

Various embodiments will now be described in detail with reference to the drawings, wherein like reference numerals identify similar or identical elements. As commonly known, the term "clinician" refers to a doctor, a nurse, or any other care provider and may include support personnel. Additionally, the term "proximal" refers to the portion of structure that is closer to the clinician and the term "distal" refers to the portion of structure that is farther from the clinician. Further still, directional terms such as front, rear, upper, lower, top, bottom, and the like are used simply for convenience of description and are not intended to limit the disclosure attached hereto.

In the following description, well-known functions or constructions are not described in detail to avoid obscuring the present disclosure in unnecessary detail.

With reference to FIGS. 1A to 4C, a fixation assembly 1 includes a post 10, a snap ring 20 formed of any suitable flexible material (e.g., compressible to temporarily reduce a diameter thereof), and a tapered cannula 30 that couple together for securement of fixation assembly 1 to osseous tissue.

Figure 1B:
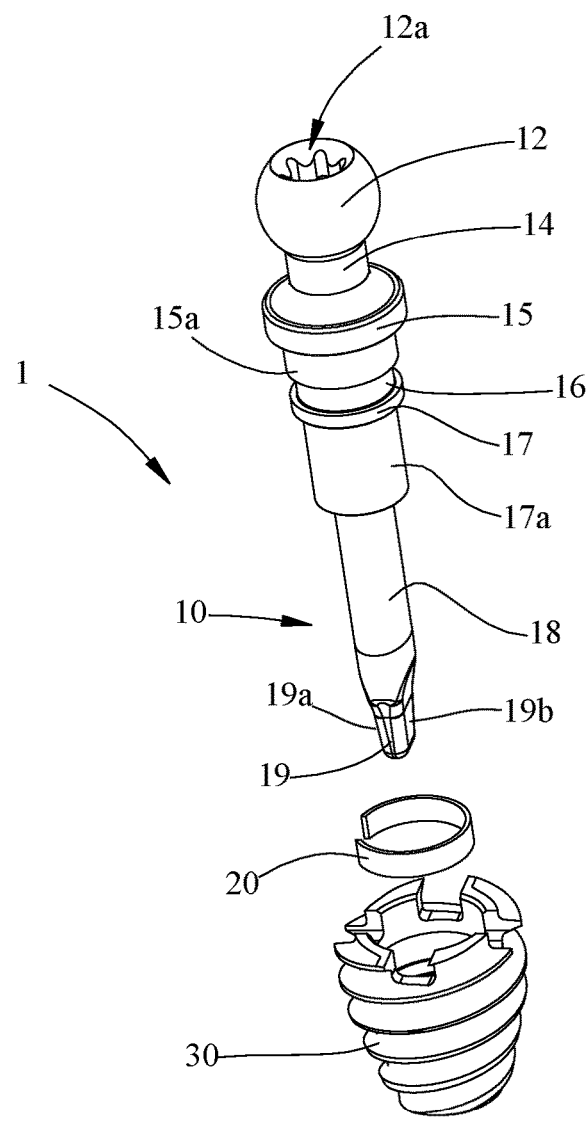
FIG. 1B is an isometric view, with parts separated, of the fixation assembly of FIG. 1A.

As shown in FIGS. 1A and 1B, post 10 of fixation assembly 1 includes a head 12 supported on a proximal end portion of post 10, a neck 14 that extends distally from head 12, a proximal ledge 15 supported on a distal end portion of head 12, a distal ledge 17, an external ring groove 16 defined between proximal and distal ledges 15, 17, a shank 18 that extends distally from distal ledge 17, and a distal tip 19 supported a distal end portion of shank 18.

Although head 12 of post 10 is illustrated as having a bulbous shape, such as spherical or semi-spherical, head 12 may have any suitable configuration. In some embodiments, head 12 of post 10 can be a threaded arm or post configured to receive mechanical hardware such as a nut (not shown). Head 12 can be configured, for example, to receive a taper lock and/or setscrew type rod-receiving housing assembly 50 (see FIG. 4C) thereon to enable such screw assembly to move relative to head 12 through a range of motion along different axes (e.g., polyaxial movement). For a more detailed description of example taper lock and/or set screw type rod-receiving housing assemblies, reference can be made to U.S. Pat. Nos. 8,814,919 and 9,393,049, the entire disclosures of each of which are incorporated by reference herein.

An outer surface of head 12, or portions thereof, maybe smooth and/or roughened (e.g., knurled). Head 12 also defines a keyed recess 12a in a proximal surface thereof that is configured to receive and engage a tool, such as a driver 200 (see FIGS. 5A and 5B) for controlling and/or manipulating post 10 upon insertion of fixation assembly 1 into osseous tissue. Keyed recess 12a may have any suitable configuration, such as a hexolobular configuration or the like.

As seen in FIG. 1B, proximal ledge 15 of post 10 includes a distal skirt 15a that extends therefrom, and distal ledge 17 of post 10 includes a distal skirt 17a that extends therefrom. Ring groove 16 of post 10 is defined between, and recessed from, a distal surface of distal skirt 15a of proximal ledge 15 and a proximal surface of distal ledge 17. External ring groove 16 is configured to receive and support snap ring 20 therein.

Referring to FIGS. 3A, 3B, 4A, and 4B, post 10 of fixation assembly 1 includes a plurality of different cross-sections along a length thereof and may have diameters that range from about 2 to about 5 mm, and most preferably between about 3 mm to about 5 mm. For instance, distal skirt 17a has a circular-cross section and is positioned to mount post 10 within tapered cannula 30. Shank 18 includes an elliptical cross-section that is configured to be received through an elliptical passage "E" formed through an isthmus "I" of a pedicle "P" of vertebral body "V" (e.g., through lumen with elliptical cross-section that is naturally formed between hard cortical tissue "H" of pedicle "P"). Shank 18 is configured to facilitate insertion of post 10 along elliptical passage "E" defined through cortical tissue "H" of the vertebral body "V" and into soft cancellous tissue "S" of the vertebral body "V." Shank 18 is positioned to extend distally beyond tapered cannula 30 when proximal portion 17a of post 10 is mounted to tapered cannula 30. Shank 18 may extend at least a quarter of a length of post 10. In some embodiments, shank 18 may extend at least a half of the length of post 10. An outer surface of shank 18 may be smooth to facilitate passage through vertebral body "V." In some embodiments, outer surface of shank 18 may be roughened (e.g., knurled, ridges, etc.) and/or threaded (e.g., one or more shallow helical threads, or portions thereof) to facilitate gripping to osseous tissue. Distal tip 19 of shank 18 has a tapered configuration with oppositely-oriented flat surfaces 19a, 19b thereon to facilitate insertion of shank 18 into the cancellous tissue "S."

Figure 2A:
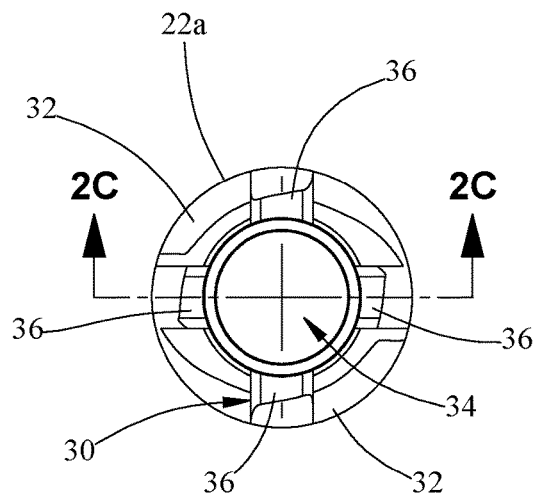
FIG. 2A is a top view of a cannula of the fixation assembly of FIGS. 1A and 1B.
Figure 2B:
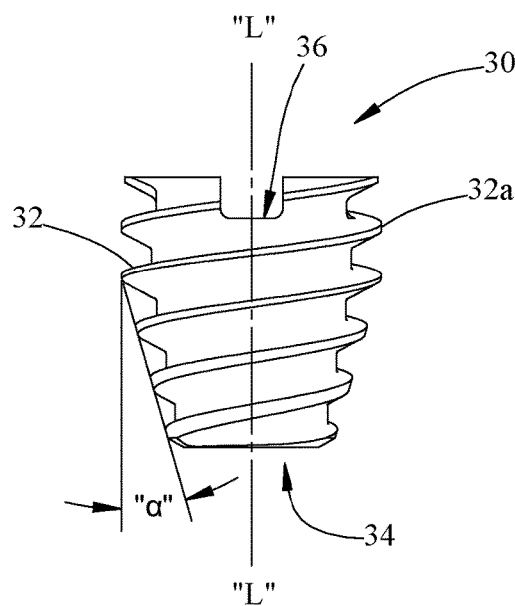
FIG. 2B is a side view of the cannula of FIG. 2A.
Figure 2C:
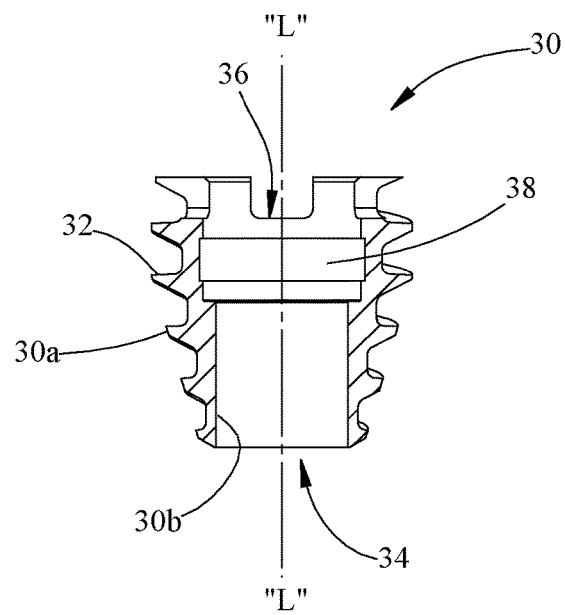
FIG. 2C is a longitudinal cross-sectional view of the cannula of FIGS. 2A and 2B as taken along section line 2C-2C shown in FIG. 2A.
Figure 3A:
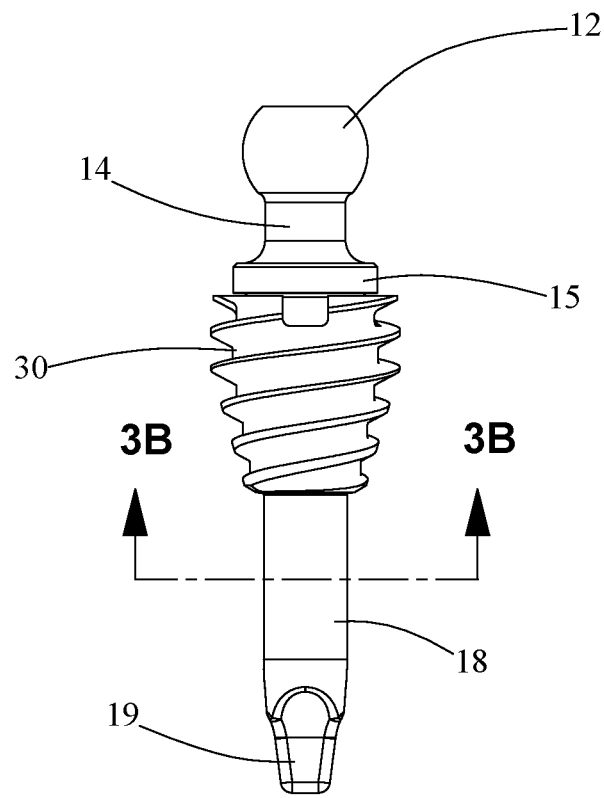
FIG. 3A is a front view of the fixation assembly of FIG. 1A.
Figure 3B:
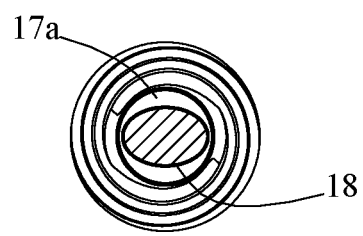
FIG. 3B is cross-sectional view of the fixation assembly as taken along section line 3B-3B shown in FIG. 3A.

As seen in FIGS. 2A-2C, tapered cannula 30 of fixation assembly 1 is configured to fit proximal and adjacent to the isthmus "I" of the pedicle "P" of a vertebral body "V" and is configured to limit insertion depth of post 10 of fixation assembly 1 when fixation assembly 1 is secured to a vertebral body "V."

Tapered cannula 30 includes a thread 32 that extends along (e.g., clockwise and/or counterclockwise) an outer surface 30a thereof to facilitate engagement with osseous tissue. Thread 32, which may be helical, can include sharpened edges 32a configured to cut into osseous tissue. In embodiments, a major diameter of tapered cannula 30 (e.g., thread 32) may be in the range of about 9 mm to about 13 mm, and most preferably 10-12 mm. Tapered cannula 30 includes a proximal to distal taper, along at least a distal portion thereof, which may be sloped at any suitable angle of taper "a" relative to a central longitudinal axis "L-L" defined therethrough, so that tapered cannula 30 can fit within or stay partially above the isthmus "I" of the pedicle "P." Tapered configuration of tapered cannula 30 is configured to limit and/or prevent proximal portions of post 10 of fixation assembly 1 from breaching osseous tissue of the vertebral body "V" when fixation assembly 1 is mounted to the vertebral body "V." In some embodiments, the major diameter of tapered cannula 30 may taper along the length of tapered cannula 30, at a ratio of major diameter proximal to major diameter distal, in the range of 1-2, most preferably 1.4-1.7. In some embodiments, the angle of the taper "a" may vary from about 10 to about 60 degrees, and most preferably from about 18 to about 56 degrees.

In some embodiments, tapered cannula 14 can extend at least a half of a length of post 10, and more preferably, less than a quarter of a length of post 10.

An inner surface 30b of tapered cannula 30 defines a central bore 34 that extends through tapered cannula 30 and is positioned to receive shank 18 of post 10 therethrough. A proximal end portion of tapered cannula 30 is positioned to engage a bottom surface of ledge 15 of post 10 to help limit distal advancement of post 10 through tapered cannula 30 and prevent head 12 of post 10 from passing through central bore 34 of tapered cannula 30 (see FIG. 1A). Inner surface 30b of tapered cannula 30 also defines an internal ring groove 38 therein. Internal ring groove 38 of tapered cannula 30 is configured to receive and support snap ring 20 therein. Internal ring groove 38 of tapered cannula 30 is also configured to align with external ring groove 16 of post 10 when post 10 is positioned within tapered cannula 30. Snap ring 20 is configured to help retain post 10 and tapered cannula 30 in an axially fixed relationship with respect to one another when snap ring 20 is positioned within internal ring groove 38 of tapered cannula 30 and external ring groove 16 of post 10. For instance, once snap ring 20 is simultaneously expanded into ring grooves 16, 38 of post 10 and tapered cannula 30, respectively, snap ring 20 prevents post 10 from backing out from tapered cannula 30 (proximally relative to tapered cannula 30) and advancing farther into tapered cannula 30 (distally relative to tapered cannula).

Tapered cannula 30 further includes a plurality of spaced apart cut outs 36 defined in a proximal end portion thereof. Although FIG. 2A illustrates four rectangular cut outs 36 that are 90 degrees out of phase with respect to one another, tapered cannula 30 may include any number and/or configuration of cut outs 36, one or more of which may be disposed at any suitable location around the proximal end portion of tapered cannula 30.

Figures 5A, 5B:
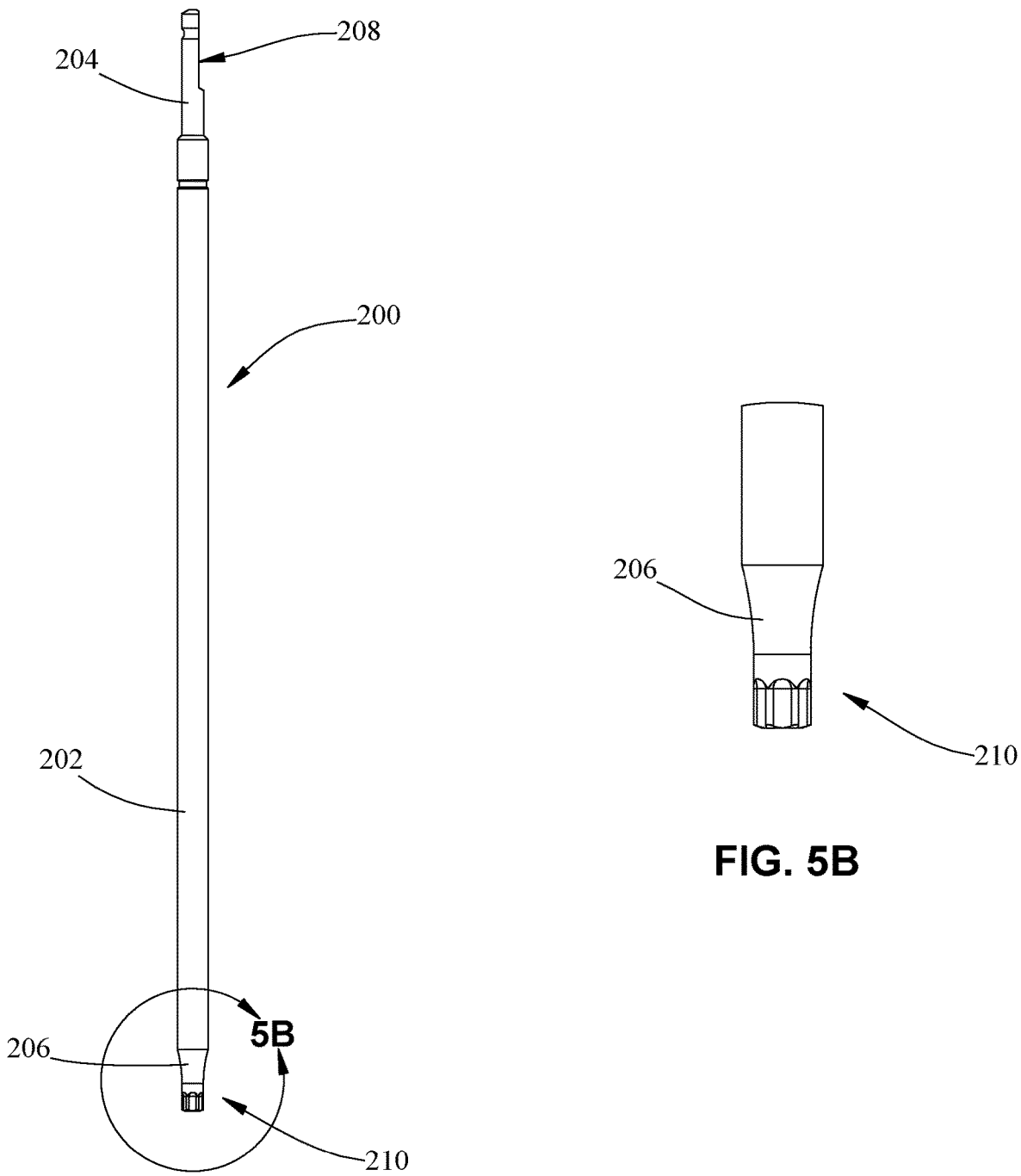
FIG. 5A is a plan view of a driving tool for facilitating securement of the fixation assembly of FIG. 1A to osseous tissue.
FIG. 5B is an enlarged view of the area of detail delineated in FIG. 5A.

With reference to FIGS. 5A and 5B, a driving tool or driver suitable for use with fixation assembly 1 is provided and generally identified by reference numeral 200. Driver 200 includes an elongated shaft 202 having a proximal portion 204 and an opposed distal portion 206. Proximal portion 204 of elongated shaft 202 defines a handle attachment feature 208 that is configured to apply a driver handle (not shown) to enable selective application of rotational force to driver 200 (e.g., a clinician grips the driver handle and applies rotational force thereto). Distal portion 206 of driver 200 tapers to a driving, but reduced diameter engagement region 210. Engagement region 210 includes protrusions and recesses that are complementary to keyed recess 12a of post 10 so that driver 200 is configured to control, and/or manipulate (e.g., selectively rotate) post 10 and/or for selectively inserting and/or removing a setscrew (e.g., for securing a spinal rod in a housing supported on fixation assembly; see, for example, U.S. Pat. No. 9,393,049 incorporated by reference herein).

Figure 6:
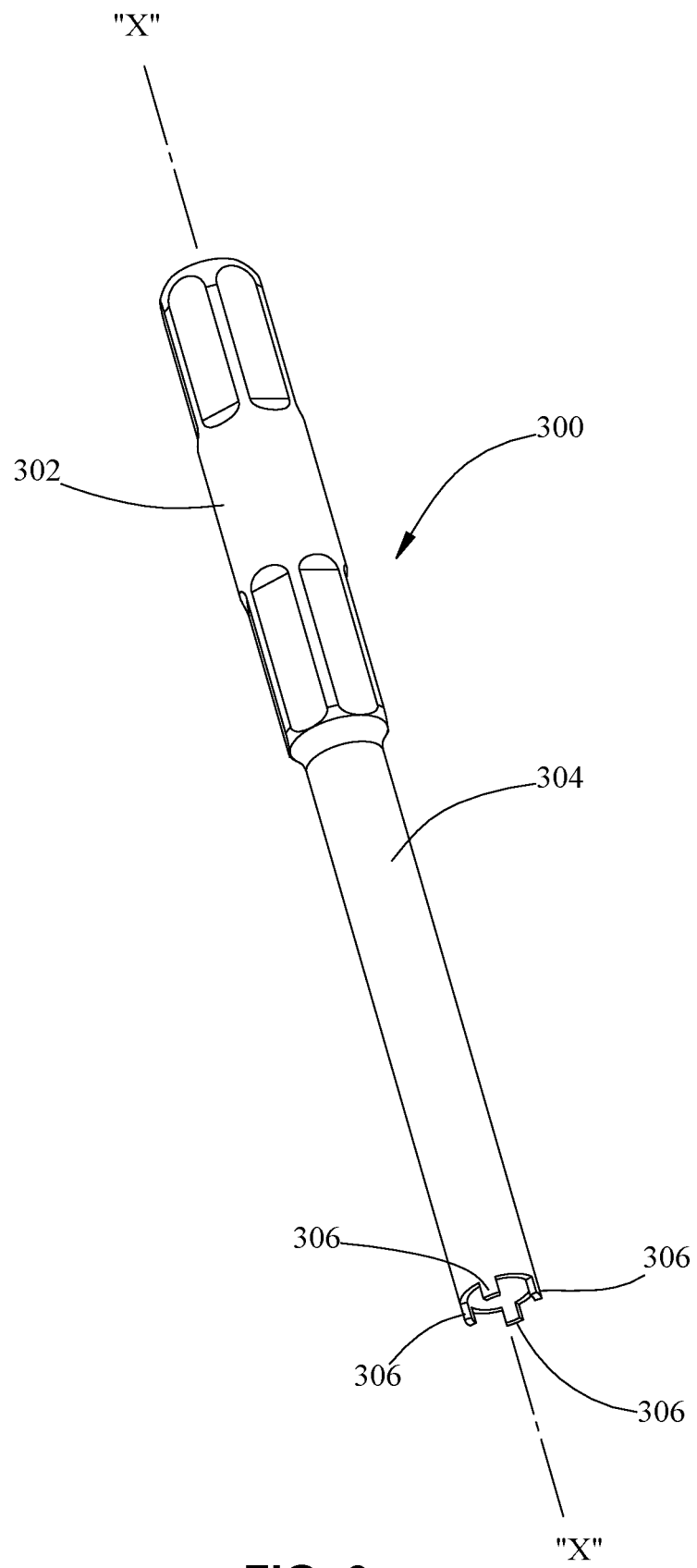
FIG. 6 is a perspective view of an inserter for facilitating securement of the fixation assembly of FIG. 1A to osseous tissue.

As seen in FIG. 6, an inserter 300 includes a handle 302 supported on a proximal end portion thereof and an elongated shaft 304 that extends distally from handle 302. Elongated shaft 304, which may have a tubular configuration, includes a plurality of spaced-apart tabs 306 (radially and/or circumferentially spaced apart) that extend distally from elongated shaft 304 to a distal end of inserter 300. The plurality of spaced-apart tabs 306 are configured to be received within cut outs 36 of tapered cannula 30, and may be complementary thereto, so that manual rotation of inserter 300 about a central longitudinal axis "X-X" thereof rotates tapered cannula 30 about a central longitudinal axis "A-A" (FIG. 1A) of post 10 for driving tapered cannula 30 into osseous tissue when inserter 300 is coupled to tapered cannula 30.

In use, referring to FIGS. 1A-6, an insertion hole is formed in a vertebral body "V," namely, in the isthmus "I" of a pedicle "P" adjacent to elliptical passage "E" thereof, using known tools and techniques (e.g., burr, awl, etc.—not shown). Then, with post 10 coupled to tapered cannula 30, post 10 is advanced into the insertion hole until tapered cannula 30 engages osseous tissue. Next, with tabs 306 of inserter 300 engaged with cut outs 36 of tapered cannula 30, inserter 300 is rotated to drive tapered cannula 30 into the hard cortical bone "H," proximal and adjacent to the isthmus "I" of the pedicle "P" by rotating tapered cannula 30 about post 10 so that thread 32 of tapered cannula 30 secures tapered cannula 30 to the cortical bone "H" proximal and adjacent to the isthmus "I." By virtue of snap ring 20 and ledge 15 of post 10 maintaining post 10 and tapered cannula 30 axially fixed, post 10 advances axially through elliptical passage "E" and into the cancellous bone tissue "S" as tapered cannula 30 advances along the cortical bone "H" towards the isthmus "I" to secure fixation assembly 1 to the vertebral body "V."

According to one aspect of the present disclosure, after an insertion hole is formed in the vertebral body "V," and before tapered cannula 30 and post 10 are coupled together, tapered cannula 30 can be driven into the hard cortical bone "H," proximal and adjacent to the isthmus "I," with inserter 300 separate from post 10. Once tapered cannula 30 is threaded to the isthmus "I," post 10 can be inserted through tapered cannula 30 (e.g., pushed) so that snap ring 20, which may be mount to either ring groove 16 of post 10 or ring groove 38 of tapered cannula 30, couples tapered cannula 30 to post 10. For instance, with snap ring 20 held within ring groove 18 of post 10, post 10 is advanced axially into tapered cannula 30, radially compressing snap ring 20 to a compressed position (temporary) between outer surfaces of post 10 and inner surfaces of tapered cannula 30, until snap ring 20 and ring grooves 18, 38 are all aligned so that snap ring 20 can expand radially outward toward an uncompressed position (permanent). In the uncompressed position, snap ring 20 holds post 10 in an axially fixed position relative to tapered cannula 14. In such an axial fixed position, tapered cannula 30 is freely rotatable (clockwise or counterclockwise) about the longitudinal axis "A-A" of post 10.

Figure 4A:
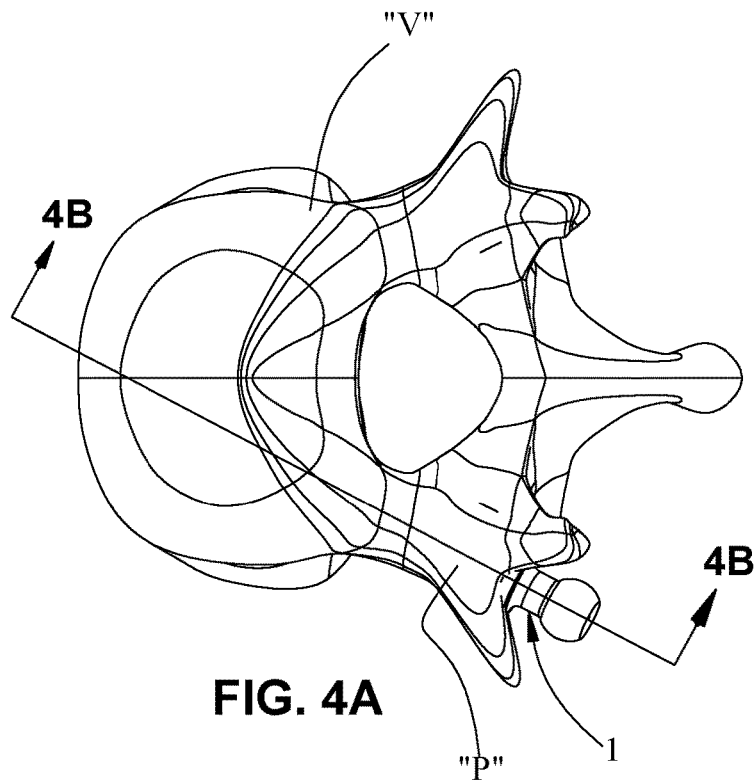
FIG. 4A is an isometric view illustrating the fixation assembly of FIG. 1A secured in osseous tissue.
Figure 4B:
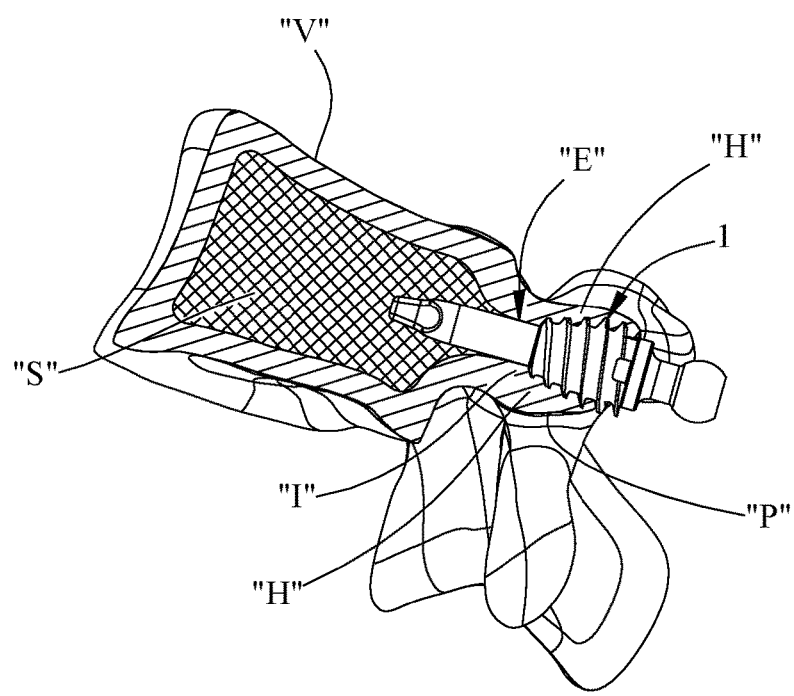
FIG. 4B is side view of FIG. 4A shown in partial cross-section for clarity.
Figure 4C:
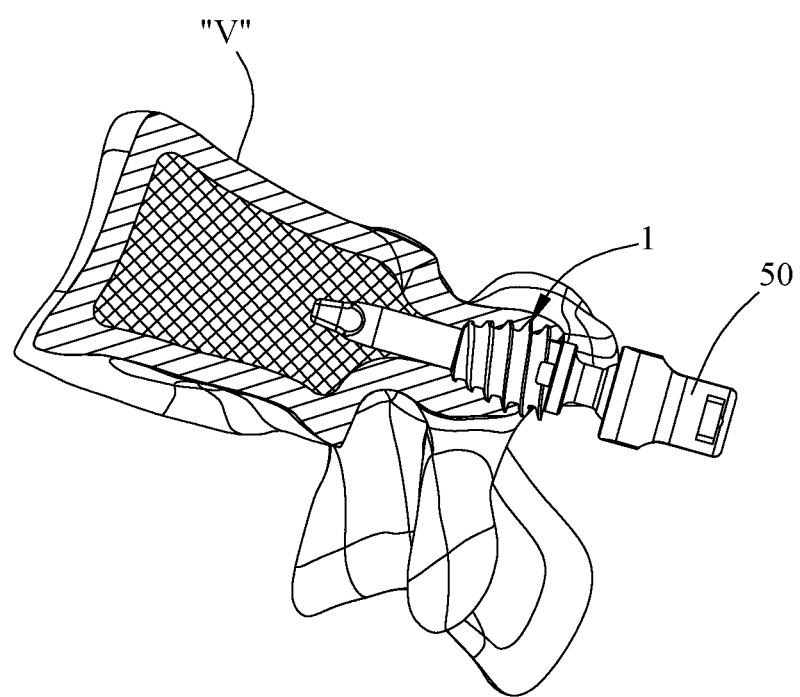
FIG. 4C is another view of FIG. 4B with a set-screw type spinal rod housing shown secured to the fixation assembly of FIG. 1A.

As seen in FIG. 4C, a taper lock or setscrew type housing 50 can be secured to fixation assembly 1 to selectively secure a spinal rod (not shown) to the vertebral body "V."

The presently disclosed fixation assembly can, in some embodiments, be included with any suitable spinal plate (not shown), for example to secure the spinal plate across one or more vertebrae. For a more detailed description of an example spinal plate, reference can be made to commonly owned U.S. Pat. No. 8,636,738, the entire disclosure of which is incorporated by reference herein.

Any of the presently disclosed embodiments, or components thereof, can be formed of any suitable biocompatible material or combinations of materials for use in surgical procedures such as mixed metallic materials like titanium, titanium alloy (e.g., Ti-6Al-4V), stainless steel, and cobalt chrome alloy.

Any of the presently disclosed embodiments, or components thereof can be formed using any suitable technique such as welding, fastening, machining, molding, etc. In some embodiments, one or more of the components can be secured together using any suitable technique such as welding, fastening, machining, molding, etc. Any of the components may be press-fit together.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A fixation assembly, comprising:
   a tapered cannula;
   a post defining a tapered distal tip and a shank having a non-threaded outer surface; and
   a snap ring attachable to the post and the tapered cannula, the snap ring configured to maintain the tapered cannula axially fixed in relation to the post such that the tapered cannula and the post are rotatable relative to each other,
   wherein when the post and the tapered cannula are axially fixed relative to one another, the tapered distal tip and at least a portion of the shank extend distally beyond a distal end of the tapered cannula.

2. The fixation assembly of claim 1, wherein the tapered cannula is threaded.

3. The fixation assembly of claim 1, wherein the post defines a first ring groove positioned to receive the snap ring therein.

4. The fixation assembly of claim 3, wherein the tapered cannula defines a second ring groove positioned to receive the snap ring therein.

5. The fixation assembly of claim 1, wherein the snap ring is formed of a flexible material.

6. The fixation assembly of claim 1, wherein the post supports a ledge configured to engage the tapered cannula to limit distal movement of the post relative to the tapered cannula.

7. The fixation assembly of claim 1, wherein the tapered cannula defines at least one cut out in a proximal end portion thereof.

8. The fixation assembly of claim 1, wherein the post includes a spherical head supported on a proximal end portion thereof.

9. The fixation assembly of claim 1, wherein the shank defines an elliptical cross-section.

10. The fixation assembly of claim 9, wherein the tapered distal tip has at least one flat surface to facilitate insertion of the shank into osseous tissue.

11. A fixation assembly comprising:
    a rod-receiving housing; and
    a fixation assembly coupled to the rod-receiving housing, the fixation assembly including:
      a tapered cannula;
      a post including a tapered distal tip and a shank defining an elliptical cross-section and a non-threaded outer surface; and
      a snap ring attachable to the post and the tapered cannula to secure the post and the tapered cannula together.

12. The fixation system of claim 11, wherein the tapered cannula is threaded.

13. The fixation assembly of claim 11, wherein the post defines a first ring groove positioned to receive the snap ring therein.

14. The fixation assembly of claim 13, wherein the tapered cannula defines a second ring groove positioned to receive the snap ring therein.

15. The fixation assembly of claim 11, wherein the snap ring is formed of a flexible material.

16. The fixation assembly of claim 11, wherein the post supports a ledge configured to engage the tapered cannula to limit distal movement of the post relative to the tapered cannula.

17. The fixation assembly of claim 11, wherein the tapered cannula defines at least one cut out in a proximal end portion thereof.

18. The fixation assembly of claim 11, wherein the post includes a spherical head supported on a proximal end portion thereof.

19. A method for securing a fixation assembly to osseous tissue, the method comprising:
    securing a tapered cannula to an isthmus of a pedicle;
    pushing a post through the tapered cannula and the isthmus of the pedicle, the post defining a tapered distal tip and a shank having a non-threaded outer surface; and
    axially fixing the post to the tapered cannula with a snap ring such that the tapered distal tip and at least a portion of the shank extend distally beyond a distal end of the tapered cannula.

* * * * *